United States Patent [19]

Tulis

[11] 3,939,971

[45] Feb. 24, 1976

[54] STERILANT PACKAGE ASSEMBLY

[75] Inventor: Jerry J. Tulis, Raleigh, N.C.

[73] Assignee: Becton, Dickinson and Company, Rutherford, N.J.

[22] Filed: Feb. 13, 1973

[21] Appl. No.: 332,215

[52] U.S. Cl. ............ 206/205; 21/DIG. 4; 206/210; 206/363; 206/484; 229/56; 426/133
[51] Int. Cl.² .................. B65D 31/12; B65D 81/24
[58] Field of Search ............ 21/85, 88, 89, DIG. 4; 206/43, 46 ST, 46 PV, 63.2 R, 210, 339, 363, 370, 438, 439, 484, 205; 426/112, 124, 133, 316, 326, 394, 410, 418, 419; 229/56

[56] References Cited
UNITED STATES PATENTS

| | | | |
|---|---|---|---|
| 2,714,557 | 8/1955 | Mahaffy | 229/56 UX |
| 2,998,880 | 9/1961 | Ladd | 206/63.2 R |
| 3,114,599 | 12/1963 | Fanning | 21/DIG. 4 |
| 3,323,640 | 6/1967 | Kugler | 206/205 |
| 3,435,948 | 4/1969 | Kaganov et al. | 206/439 |
| 3,476,506 | 11/1969 | Andersen et al. | 21/DIG. 4 |
| 3,494,726 | 10/1970 | Barasch | 21/DIG. 4 |
| 3,503,497 | 3/1970 | Riely | 206/365 X |
| 3,507,386 | 4/1970 | Ishii et al. | 206/63.2 R |
| 3,625,353 | 12/1971 | Ishii | 206/365 |
| 3,670,874 | 6/1972 | Brunner | 206/205 |

*Primary Examiner*—George E. Lowrance
*Assistant Examiner*—Steven E. Lipman
*Attorney, Agent, or Firm*—Marn & Jangarathis

[57] ABSTRACT

A package for sterilizing implements at a remote time and location is provided which package is formed of at least two compartments separated by a thin semi-permeable wall. The first compartment is provided to receive an implement to be sterilized therein with the second sealed compartment being provided with a substrate having a thermally-activated or releasable sterilizing gas bonded thereto. Upon release, the sterilizing gas permeates the thin semi-permeable wall to effect sterilization of the implement.

12 Claims, 4 Drawing Figures

STERILANT PACKAGE ASSEMBLY

BACKGROUND OF THE INVENTION

This invention relates to a package for implements including the provision for the sterilization thereof, and more particularly to a package for a medical or surgical implement which may be sterilized at a time and location remote from the packaging thereof.

The need for sterilized implements in remote locations has in recent years focussed attention on the manner of packaging these implements. For instance, the requirement that a surgical implement be sterile at the time of use in a remote location after considerable time has elapsed since packaging without the necessity of providing expensive and immobile sterilization equipment, is felt in military field use, industrial applications, etc. In U.S. Pat. No. 3,494,726, to Barasch, and assigned to the same assignee as the instant invention, there is disclosed a package and method for remote sterilization which is achieved by placing a surgical instrument in an enclosed package impervious to bacterial contaminants and containing therein a sterilizing gas releasably bonded to a substrate. By the application of heat, the sterilizing gas is released and sterilization of the surgical instrument effected at the remote location.

Although, in the aforementioned U.S. patent, sterilization of a surgical instrument by release of a sterilizing gas is provided, certain problems are encountered. One problem occurs during the period the surgical instrument is stored in the package. During this period, water vapor from the substrate can result in a deleterious effect, e.g. forming rust on the implement. Another problem is possible deleterious effects produced by the formation of a film of the sterilant on the instrument.

OBJECTS OF THE INVENTION

An object of this invention is to provide an improved sterilizing package.

A further object of this invention is to provide an improved disposable sterilizing package which permits the sterilization of an implement contained therein at a remote time and location.

A still further object of this invention is to provide an improved sterilizing package which is safe and non-toxic and which permits the use of a heat-releasable sterilizing gas within the package under controlled conditions.

SUMMARY OF THE INVENTION

These and other objects of the invention are achieved by a package formed of thick plastic outer walls of a thickness impervious to bacterial contamination, in which package at least two separate and distinct compartments are defined by a thin inner semi-permeable wall of a thickness pervious to the passage of a sterilizing gas but substantially impervious to the passage of water vapor. One compartment is adapted to receive an implement with the other compartment adapted to receive a substrate having a thermally-activated or releasable sterilizing gas bonded thereto.

BRIEF DESCRIPTION OF THE DRAWINGS

The invention will now be described with reference to the accompanying drawings wherein like reference numerals are used throughout and wherein.

DETAILED DESCRIPTION OF THE INVENTION

Figure 1:
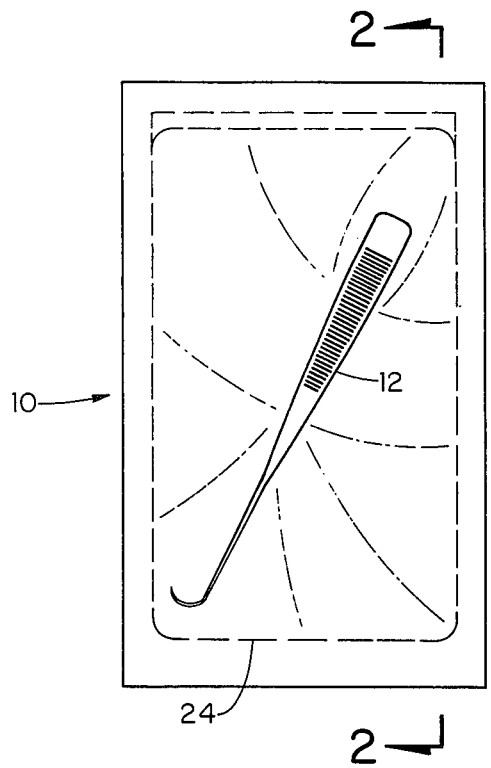
FIG. 1 is a front view of a sterilizing package illustrating one embodiment of the present invention.
Figure 2:
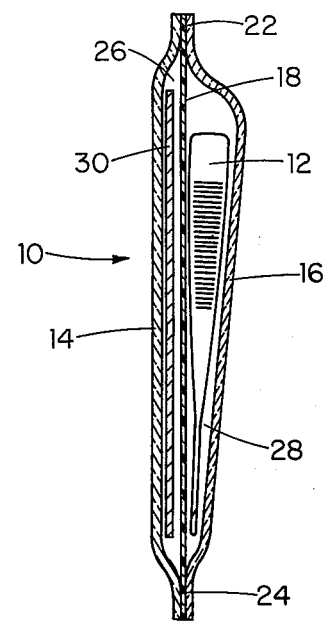
FIG. 2 is a cross-sectional side view of the sterilizing package shown in FIG. 1, and taken along line 2—2 thereof.

Referring now to FIGS. 1 and 2 there is provided a package, generally indicated at 10, formed of thick outer walls 14 and 16 and a thin inner wall 18. Outer walls 14 and 16 and inner wall 18 sandwiched therebetween are sealed together at 24 as shown by the single dotted line in FIG. 1, such as by heat sealing techniques, to form compartments 26 and 28. The compartment 28 formed by outer wall 14 and inner wall 18 is adapted to receive a substrate 30 containing a thermallyactivated or releasable sterilizing gas bonded thereto. The compartment 28 formed by outer wall 16 and inner wall 18 is adapted to receive an implement to be sterilized, such as surgical instrument 12, it being understood that the function of each compartment is interchangeable. Compartments 26 and 28 are enclosed by a seal means of the package along double dotted line 24, such as by heat sealing techniques.

The outer walls 14 and 16 are formed of a thermoplastic material, such as polyethylene, having a thickness of about 4 to 6 mils, and impervious to the sterilizing gas. The inner wall 18 is made of a similar type of thermoplastic material having a thickness of about 0.5 to 1.5 mils, and pervious to the passage of the sterilizing gas yet substantially impervious to the passage of water vapor.

The sterilizing gases to be used with the instant invention include the known gaseous sterilants, such as formaldehyde, ethylene oxide, betapropiolactone, propylene oxide and phenol. The sterilizing gases are bonded physically to non-flowable substrates or carriers, either solid or viscous pastes, such as activated alumina (such as used in chromatographic columns and sold under the laboratory name, such as CENCO); silica gels (activation optional); activated charcoal or celluloses (such as blotting paper or methylcellulose); or other substrates capable of forming a releasable bond with the sterilizing substance, such as methylene glycol-starch, methylene glycolmelamine, methylene glycolethanolamine or paraformaldehyde (heated), said bonds being weak to enable release of the sterilizing gas when desired. The bonds, as noted, may be either physical bonds or chemical bonds and capable of breaking by thermal energy to cause diffusion of the sterilizing gas, either at ambient or slightly higher temperatures. Bonds capable of such breakage are usually weaker than about 10 kilocalories per mole. However, in the case of stronger bonds, such bonds may be broken and cause release of the gas by a shift of equilibrium brought about by a change in temperature or concentration or by the action of a catalyst. The catalyst employed, if any, may be any suitable acid which will not be harmful in the environment, such as for example, citric, gluconic and phosphoric acids.

Sterilization of the surgical instrument 12 is effected, for example, by subjecting the package 10 to thermal energy to cause release of the sterilizing gas from the substrate 30 throughout compartment 26. The thin inner wall 18 is pervious thereto and allows the sterilizing gas to readily diffuse therethrough and enter compartment 28 to thereby effect sterilization of the surgical instrument 12 after a period of time. The thin inner wall 18 does not permit water vapor to diffuse therethrough during the storage period thereby substantially eliminating the potential deleterious effect upon a metallic instrument.

Figure 3:
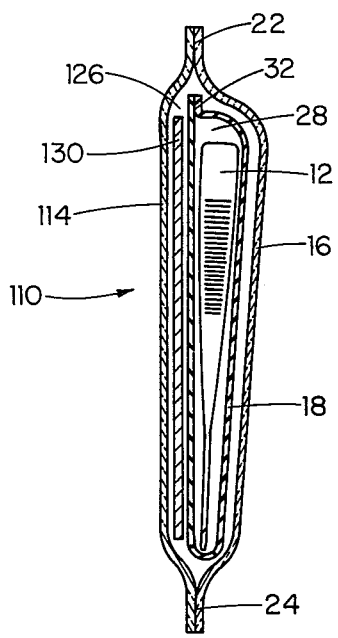
FIG. 3 is a cross-sectional side view of another embodiment of the instant invention.

Another embodiment of the present invention is shown in FIG. 3 wherein like reference numerals are used to denote like elements and wherein a package, generally indicated as 110, is formed by circumferentially sealing two thick thermoplastic outer walls 114 and 116 to form a compartment 126 in which is disposed an inner package, generally indicated as 140, and a substrate 130 containing a thermally-activated or releasable sterilizing gas bonded thereto. The inner package 140 is formed by sealing, for example, two thermoplastic films 118 about a surgical instrument 112 within compartment 128. The thermoplastic walls 118 are pervious to a sterilizing gas but substantially impervious to water vapor. It will be understood that the outer package may be formed by sealing a portion of the outer walls 118 whereupon the inner package 140 and substrate 138 are inserted prior to the sealing of the remaining portions of the outer walls 118. It will be apparent that sterilization of the instrument 112 is effected in the same manner to yield the same results as the embodiment of FIG. 2.

Figure 4:
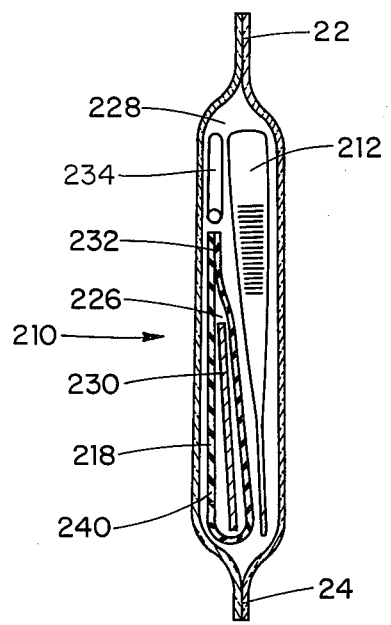
FIG. 4 is a cross-sectional side view of still another embodimennt of the instant invention.

Still another embodiment of the present invention is shown in FIG. 4 wherein like reference numerals are used to denote like elements. A package 210 is formed by circumferentially sealing two thick thermoplastic outer walls 214 and 216 to form a compartment 228 in which is disposed a smaller thermoplastic package 240, a surgical instrument 212, and a glass vial 234. The inner package 240 is formed by circumferentially sealing, for example, two thermoplastic walls 218 about a substrate 130 containing a thermallyactivated releasable sterilizing gas bonded thereto. The wall 218 is pervious to sterilizing gas but impervious to water vapor. The glass vial 234 contains a neutralizing substance, such as ammonia.

Upon subjecting the package 210 to a source of thermal energy as hereinabove described the requisite sterilization of the instrument is effected. To minimize the escape of toxic vapors from the package 10 upon opening, the glass vial 228 is thereafter broken thereby releasing ammonia which neutralizes the sterilizing gas. It is apparent that a greater duty of care is required for the handling and storage of the embodiment of FIG. 4 to prevent premature breakage of the glass vial.

While the present invention has been described with reference to a disposable sterilizing package, including an implement to be sterilized, it is understood that the package may be formed with an essentially vapor tight slide fastening means which would permit the reuse thereof. Thus, after use, the package would be reopened and the implement removed with the spent substrate being replaced with a fresh substrate for subsequent activation when sterilization of another implement is desired. In addition, the package may be formed with the sterilant carrying substrate sealed therein prior to its intended use. Thus, the sterilizing package could be stored or shipped and when needed, the instrument to be sterilized is sealed in the compartment and the package exposed to the necessary thermal energy for release of the sterilizing gas.

While the invention has been discussed with reference to the use of a polyethylene film, it is understood that other thermoplastic films may be used, such as the polyvinyl chlorides, polyvinyl acetates, polyvinyl styrenes, as well as thermosetting films provided the thickness thereof is selected to provide the desired permeability to the sterilizing gas and the substantial nonpermeability to water vapor.

While the invention has been described in connection with several exemplary embodiments thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed is:

1. A package for sterilizing implements comprised of two gas impermeable outer walls and an inner wall sandwiched therebetween thereby forming two compartments, said inner wall being pervious to sterilizing gas but impervious to water vapor.

2. The package as defined in claim 1 wherein said outer walls and said inner wall are formed of a thermoplastic material.

3. The package as defined in claim 2 wherein said outer walls are of a thickness of 4 to 6 mils and said inner wall is of a thickness of 0.5 mils to 1.5 mils.

4. The package as defined in claim 1 wherein one of said compartments is sealed and has contained therein a substrate including a controllably releasable sterilizing gas bonded thereto.

5. The package as defined in claim 1 wherein both of said distinct compartments are sealed enclosures, and one of said compartments contains a substrate including a controllably releasable sterilizing gas bonded thereto, and said other compartment contains a surgical implement.

6. A package as defined in claim 5 wherein the compartment containing a surgical implement has contained therein a glass vial of ammonia gas.

7. A package for sterilizing implements comprised of a first compartment defined by outer walls of a thermoplastic material of a sufficient thickness to render the walls gas impermeable and a thin walled inner package of a thermoplastic material forming a second compartment which is pervious to sterilizing gas but impervious to water vapor.

8. The package as defined in claim 7 wherein the compartment formed by said inner package is a sealed enclosure and contains therein an implement to be sterilized, and said outer package forms a sealed enclosure containing said inner package and a substrate including a controllably releasable sterilizing gas bonded thereto.

9. The package as defined in claim 7 wherein said thin walled inner package forms a sealed enclosure and contains a substrate including a controllably releasable sterilizing gas bonded thereto.

10. The package as defined in claim 9 wherein said outer package is sealed and has contained therein said inner package and a surgical implement.

11. The package as defined in claim 10 wherein the outer package containing said surgical implement and said inner package further contains a glass vial of ammonia gas.

12. The package as defined in claim 11 wherein said thermoplastic materials are polyethylene.

* * * * *